US00PP09958P

United States Patent [19]

Cornelis

[11] Patent Number: Plant 9,958

[45] Date of Patent: Jul. 8, 1997

[54] SPATHIPHYLLUM PLANT NAMED MAX

[75] Inventor: Daniel Cornelis, Merelbeke, Belgium

[73] Assignee: Milestone Agriculture, Inc., Apopka, Fla.

[21] Appl. No.: 628,951

[22] Filed: Apr. 8, 1996

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—C. A. Whealy

[57] ABSTRACT

A distinct cultivar of Spathiphyllum plant named Max, characterized by its large leaves that are upright, glossy and dark green in color; large plants suitable for large containers; strong and vigorous growth habit; numerous large flowers held just above the foliage on strong and erect peduncles; and large, pure white, flat spathes and long spadices.

1 Drawing Sheet

The present invention relates to a new and distinct cultivar of Spathiphyllum plant, botanically known as Spathiphyllum, and hereinafter referred to by the cultivar name Max.

The new cultivar is a product of a planned and controlled breeding program conducted by the inventor in Merelbeke, Belgium. The new cultivar originated from a deliberate cross by the inventor between the Spathiphyllum cultivar Sensation (not patented) as the female or seed parent and the Spathiphyllum cultivar Daniel (disclosed in U.S. Pat. No. P.P. 8,655) as the male or pollen parent. The cultivar Max was discovered and selected by the inventor as a plant within the progeny of the stated cross in a controlled environment in Merelbeke, Belgium.

Asexual propagation, by division, of the new cultivar at Merelbeke, Belgium, has shown that the unique features of this new Spathiphyllum plant are stabilized and reproduced true to type in successive generations of asexual propagation.

The new Spathiphyllum has not been observed under all possible environmental conditions. The phenotype may vary somewhat with variations in environment such as temperature and light intensity, without, however, any variance in genotype. The following observations, measurements and comparisons describe plants grown in Kwintsheul, The Netherlands in 21-cm containers in a glass greenhouse with an average day temperaure of 22 C., and average night temperature of 20 C., and a light level of 200 to 225 lux.

The following traits have been repeatedly observed and are determined to be the unique characteristics of Max. These characteristics in combination distinguish Max as a new and distinct cultivar:

1. Large leaves that are upright, glossy and dark green in color.

2. Large plants suitable for large containers, strong aand vigorous growth habit.

3. Numerous large flowers held just above the foliage on strong and erect peduncles.

4. Large, pure white, flat spathes and long spadices.

The new Spathiphyllum can be compared to its seed parent cultivar, the cultivar Sensation, and is different from the cultivar Sensation in the following characteristics:

1. Plants of the cultivar Max are shorter than plants of the cultivar Sensation.

2. Mature leaves of plants of the cultivar Max are glossier, darker green, more narrow and smaller than mature leaves of plants of the cultivar Sensation.

3. Leaves of plants of the cultivar Max have shorter Petioels than plants of the cultivar Sensation.

4. Plants of the cultivar Max flower have smaller flowers than plants of the cultivar Sensation.

5. Plants of the cultivar Max have shorter flower peduncles than plants of the cultivar Sensation and flowers on plants of the cultivar Max are positioned just above the foliage whereas flowers on plants of the cultivar Sensation are positioned much higher above the foliage.

The new Spathiphyllum can be compared to its pollen parent cultivar, the cultivar Daniel, and is different from the cultivar Daniel in the following characteristics:

1. Plants of the cultivar Max are taller and more vigorous than plants of the cultivar Daniel. 2. Leaves of plants of the cultivar Max are larger and darker green than leaves of the cultivar Daniel.

3. Leaves of plants of the cultivar Max have an entire margin whereas leaf margins on plants of the cultivar Daniel are slightly toothed.

4. Plants of the cultivar Max have larger flowers than plants of the cultivar Daniel.

The accompaning colored photograph illustrates the overall appearance of the new cultivar, showing the colors as true as it is reasonably possible to obtain in colored reproductions of this type. The photograph comprises a top perspective view of a typical potted plant of Max.

In the following description, color references are made to The Royal Horticultural Society Colour Chart except where general terms of ordinary dictionary significance are used.

Botanical classification: Spathiphyllum cultivar Max.

Parentage:

*Seed or female parent.*—Spathiphyllum cultivar Sensation.

*Pollen or male parent.*—Spathiphyllum cultivar Daniel (U.S. Pat. No. P.P. 8,655).

Propagation: By divisions or by tissue culture.

Plant description:

*Plant shape.*—Upright, inverted triangle, symmetrical.

*Growth habit.*—Erect when young, becoming outwardly arching as leaves develop. Large plants, appropriate for 21-cm containers.

*Plant height.*—90 to 115 cm from soil level to top of leaf plane.

*Plant vigor.*—Rapid growth rate, vigorous.

*Crop time.*—Ten months are usually required from planting of a young plant to a finished 21-cm container.

*Rooting habit.*—Freely branching, numerous fleshy roots with finer lateral roots.

*Foliage description.*—Leaf shape: Young: Narrowly elliptic Mature: Elliptic. Leaf length: About 50 cm. Leaf width: About 21 cm. Margin: Entire. Leaf surface: Flat. Leaf tip: Acuminate. Leaf base: Obtuse. Leaf aspect: Mature leaves held upright and outward at a 110 to 120° angle to petiole. Leaf texture: Leathery, smooth, glabrous. Leaf color: Young, top side: 144A, glossy. Young, under side: 146D. Mature, top side: 147A, glossy. Mature, under side: 137B. Petiole length, primary shoot: 60 to 75 cm. Petiole diameter, primary shoot, just below geniculum: About 10 mm. Geniculum diameter, primary shoots: About 11 mm. Petiole wing, primary shoots: Apparent on lower 90% of mature leaf petiole. Petiole color: Young: 144A. Mature: Winged area: 147A. Above winged area: 137C. Geniculum: 144A. Venation: Top side: 147A, sunken. Under side: 144A, prominent.

Flower description:

*Flower arrangement.*—Large flat spathe with spadix held just above the foliage. Numerous flowers arise from leaf axils.

*Spathe.*—Shape: Elliptic. Size: Length: About 26 cm. Width: About 10 cm. Aspect: After unrolled, spathe is flat. Coor: Before unrolling: Yellow white (8D). Open flower: White (155D) and shiny, spathe becomes green with age.

*Spadix.*—Size: Length: About 10.5 cm. Diameter: About 15 mm. Color: Initially yellow white (8D), becoming more yellow (8C) and eventually green with age.

*Peduncle.*—Aspect: Strong and erect. Size: Length: 95 to 120 cm. Diameter: About 8 mm. Color: Young: 144D. Mature: 147A.

Disease resistance: No known Spathiphyllum diseases observed to date on plants grown under commecial greenhouse conditions.

Seed development: Seed development is rarely observed.

It is claimed:

1. A new and distinct cultivar of Spathiphyllum plant named Max, as illustrated and described.

* * * * *

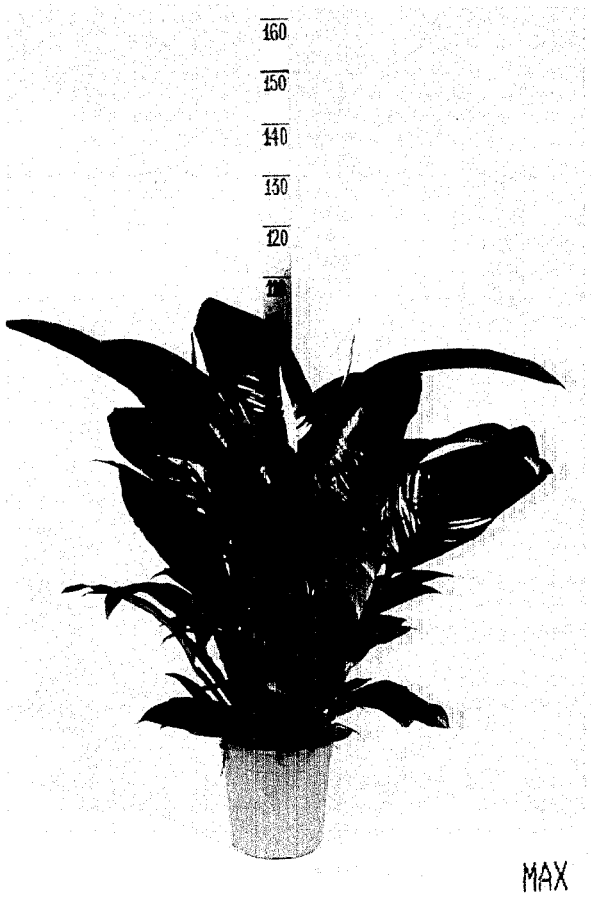
160
150
140
130
120
MAX